US012611248B2

(12) United States Patent
Shi et al.

(10) Patent No.: US 12,611,248 B2
(45) Date of Patent: Apr. 28, 2026

(54) PULSE ABLATION INSTRUMENT AND CONTROL METHOD, CONTROL APPARATUS THEREOF, ELECTRONIC DEVICE AND MEDIUM

(71) Applicant: Hangzhou Dinova EP Technology Co., Ltd., Hangzhou (CN)

(72) Inventors: Shijiang Shi, Hangzhou (CN); Kun Wang, Hangzhou (CN)

(73) Assignee: Hangzhou Dinova EP Technology Co., Ltd., Hangzhou (CN)

( * ) Notice: Subject to any disclaimer, the term of this patent is extended or adjusted under 35 U.S.C. 154(b) by 343 days.

(21) Appl. No.: 18/325,687

(22) Filed: May 30, 2023

(65) Prior Publication Data

US 2023/0301715 A1    Sep. 28, 2023

Related U.S. Application Data

(63) Continuation of application No. PCT/CN2021/134636, filed on Nov. 30, 2021.

(30) Foreign Application Priority Data

Nov. 30, 2020    (CN) .......................... 202011378682.1

(51) Int. Cl.
    *A61B 18/14*        (2006.01)
    *A61B 18/00*        (2006.01)
    *A61B 18/12*        (2006.01)
(52) U.S. Cl.
    CPC ...... *A61B 18/1492* (2013.01); *A61B 18/1206* (2013.01); *A61B 2018/00577* (2013.01); *A61B 2018/00642* (2013.01)
(58) Field of Classification Search
    CPC ............ A61B 18/1492; A61B 18/1206; A61B 2018/00577; A61B 2018/00642
    (Continued)

(56) References Cited

U.S. PATENT DOCUMENTS 5,971,980 A    10/1999  Sherman
2007/0167941 A1    7/2007  Hamel et al.
(Continued)

FOREIGN PATENT DOCUMENTS

CN    201348656    11/2009
CN    103560599    2/2014
(Continued)

OTHER PUBLICATIONS

The Extended European Search Report Dated Feb. 10, 2025 for Corresponding European Patent Application No. 21897235.4.
(Continued)

*Primary Examiner* — Beverly M Flanagan

(57) ABSTRACT

A pulse ablation instrument includes a power supply circuit, a pulse switching circuit, a sampling circuit, and a switching control circuit. The power supply circuit is configured to supply power to a load. The pulse switching circuit is connected to the power supply circuit, to regulate a current output by the power supply circuit and flowing to the load. The sampling circuit is configured to sample a current flowing through a power feeding loop of the load and obtain a sampling value. The switching control circuit is electrically connected to the sampling circuit and the pulse switching circuit, and is configured to output a drive signal which controls an operation of the pulse switching circuit according to the sampling value and reduce a duty cycle of the drive signal to reduce an output current of the power supply circuit when the sampling value is greater than a threshold value.

19 Claims, 5 Drawing Sheets

(58) Field of Classification Search
　　　 USPC ........................................................ 606/32
　　　 See application file for complete search history.

(56) References Cited

U.S. PATENT DOCUMENTS

| 2010/0179532 A1 | 7/2010 | Buysse et al. |
| 2012/0215216 A1 | 8/2012 | Friedrichs et al. |
| 2014/0276754 A1 | 9/2014 | Gilbert et al. |
| 2015/0223877 A1 | 8/2015 | Behar et al. |

FOREIGN PATENT DOCUMENTS

| CN | 104510525 | 4/2015 |
| CN | 104661384 | 5/2015 |
| CN | 109803462 | 5/2019 |
| WO | 2018/010659 | 1/2018 |

OTHER PUBLICATIONS

International Search Report and Written Opinion, issued in the corresponding PCT application No. PCT/CN2021/134636, dated Feb. 16, 2022, 8 pages.

100

100

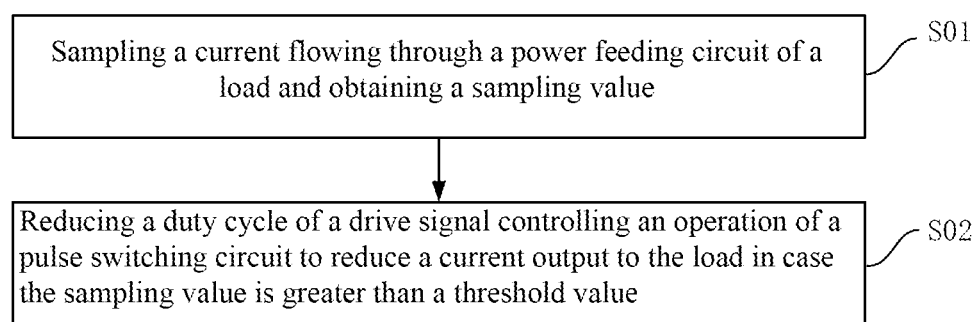

Sampling a current flowing through a power feeding circuit of a load and obtaining a sampling value ⟋ S01

Reducing a duty cycle of a drive signal controlling an operation of a pulse switching circuit to reduce a current output to the load in case the sampling value is greater than a threshold value ⟋ S02

FIG.6

Start

Read preset pulse parameter value

Control the pulse generator to output a pulse waveform according to the preset pulse parameter value Reduce a preset duty cycle value in the preset pulse parameter value and modify a register Receive and read the sampling value

Y

Sampling value reaches or exceeds a threshold value

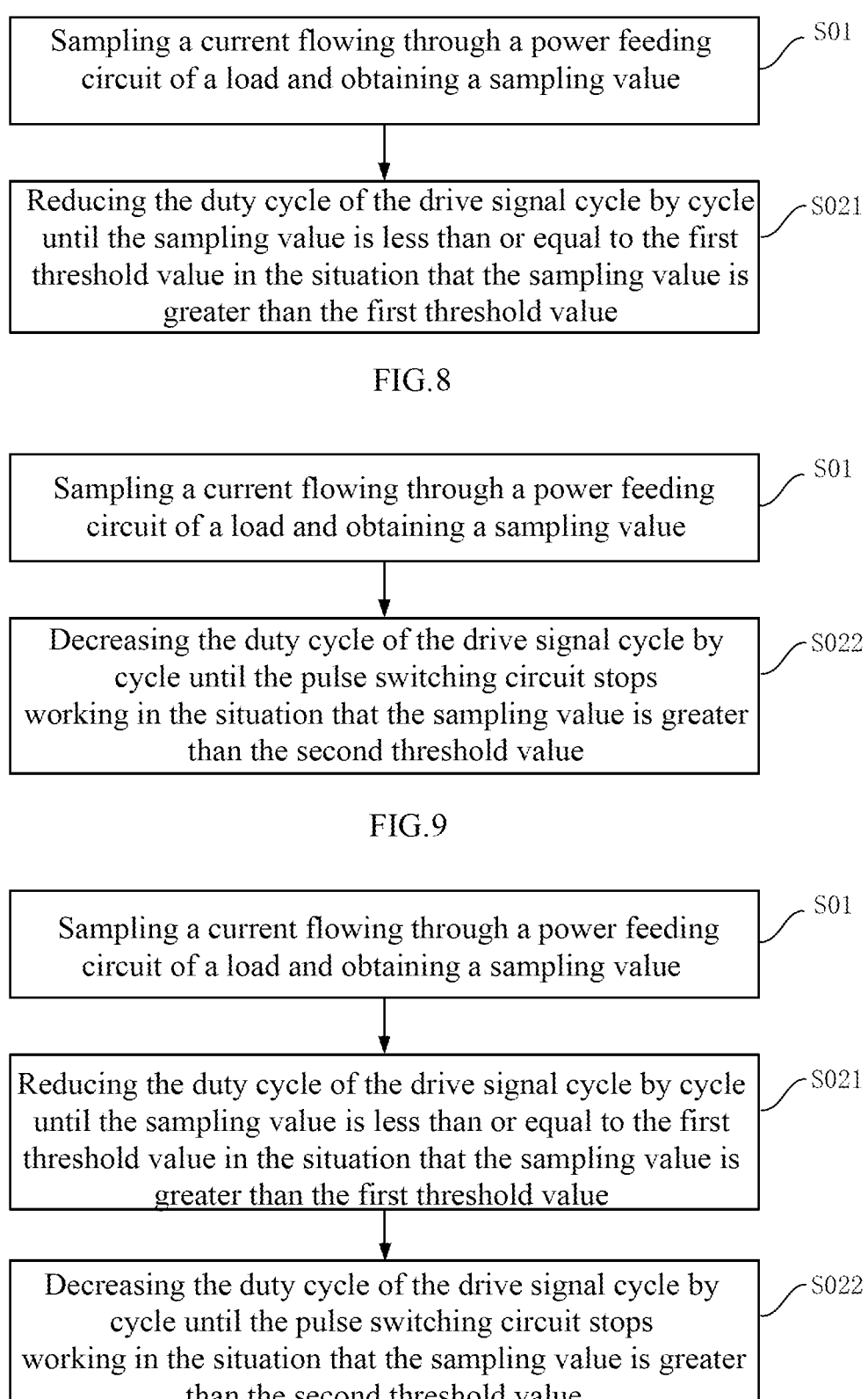

Sampling a current flowing through a power feeding circuit of a load and obtaining a sampling value          S01

Reducing the duty cycle of the drive signal cycle by cycle until the sampling value is less than or equal to the first threshold value in the situation that the sampling value is greater than the first threshold value          S021

FIG.8

Sampling a current flowing through a power feeding circuit of a load and obtaining a sampling value          S01

Decreasing the duty cycle of the drive signal cycle by cycle until the pulse switching circuit stops working in the situation that the sampling value is greater than the second threshold value          S022

FIG.9

Sampling a current flowing through a power feeding circuit of a load and obtaining a sampling value          S01

Reducing the duty cycle of the drive signal cycle by cycle until the sampling value is less than or equal to the first threshold value in the situation that the sampling value is greater than the first threshold value          S021

Decreasing the duty cycle of the drive signal cycle by cycle until the pulse switching circuit stops working in the situation that the sampling value is greater than the second threshold value          S022

FIG.10

PULSE ABLATION INSTRUMENT AND CONTROL METHOD, CONTROL APPARATUS THEREOF, ELECTRONIC DEVICE AND MEDIUM

CROSS-REFERENCE TO RELATED APPLICATIONS

The present application is a Continuation Application of PCT Application No. PCT/CN2021/134636, filed on Nov. 30, 2021, which claims the priority of Chinese Patent Application No. 202011378682.1, filed on Nov. 30, 2020, the entire contents of which are hereby incorporated by reference.

TECHNICAL FIELD

The present application relates to the technical field of pulse ablation devices, and in particular to a pulse ablation instrument and a control method, a control apparatus thereof, an electronic device, and a media.

DESCRIPTION OF THE PRIOR ART

Pulse ablation instruments may convert a mains supply to a high voltage direct current through module circuits such as a rectifier circuit, an inverter circuit, and a boost circuit and output a steep pulse through a pulse output circuit, and utilize an electroporation technology to achieve ablation of a biological tissue.

SUMMARY OF THE DISCLOSURE

The purpose of the present application is to provide a pulse ablation instrument and a control method, a control apparatus thereof, an electronic device, and a media.

Embodiment of the present application provides a pulse ablation instrument including: a power supply circuit, configured to supply power to a load; a pulse switching circuit, connected to the power supply circuit to regulate a current output by the power supply circuit and flowing to the load; a sampling circuit configured to sample a current flowing through a power feeding loop of the load and obtain a sampling value; and a switching control circuit, electrically connected to the sampling circuit and the pulse switching circuit, and configured to output a drive signal which controls an operation of the pulse switching circuit according to the sampling value and reduce a duty cycle of the drive signal to reduce an output current of the power supply circuit when the sampling value is greater than a threshold value.

Embodiment of the present application also provides a control method of a pulse ablation instrument, including steps of: sampling a current flowing through a power feeding loop of a load and obtaining a sampling value; and reducing a duty cycle of a drive signal which controls an operation of a pulse switching circuit to reduce a current output to the load when the sampling value is greater than a threshold value.

In some embodiments, the threshold value includes a first threshold value, the step of reducing a duty cycle of a drive signal which controls an operation of a pulse switching circuit when the sampling value is greater than a threshold value includes a step of reducing the duty cycle of the drive signal cycle by cycle until the sampling value is less than or equal to the first threshold value when the sampling value is greater than the first threshold value.

The present application also provides an electronic device including: a processor; and a memory configured to store executable instructions of the processor. Wherein the processor is configured to execute the executable instructions to perform the control method of a pulse ablation instrument of the above embodiments.

The present application also provides a control apparatus of a pulse ablation instrument including: a sampling module, configured to sample a current flowing through a power feeding loop of a load and obtain a sampling value; and a current control module, configured to reduce a duty cycle of a drive signal which controls an operation of a pulse switching circuit to reduce a current output to the load when the sampling value is greater than a threshold value.

The present application also provides a computer readable medium having stored a computer program thereon which, when executed by a processor, implements a control method of a pulse ablation instrument including steps of: sampling a current flowing through a power feeding loop of a load and obtaining a sampling value; and reducing a duty cycle of a drive signal which controls an operation of a pulse switching circuit to reduce a current output to the load when the sampling value is greater than a threshold value.

BRIEF DESCRIPTION OF DRAWINGS

In order to illustrate the technical solutions of the embodiments of the present invention more clearly, the accompanying drawings required in the description of the embodiments will be briefly described below, and it is apparent that the drawings in the following description are merely some embodiments of the present invention and other drawings may be obtained by an ordinary one skilled in the art according to these drawings without creative efforts.

FIG. 6 is a flowchart illustrating a control method of a pulse ablation instrument in accordance with one embodiment of the present application;

FIG. 7 is a specific flowchart illustrating a control method of a pulse ablation instrument in accordance with an embodiment of the present application;

FIG. 8 is a flowchart illustrating a control method of a pulse ablation instrument in accordance with one embodiment of the present application;

FIG. 9 is a flowchart illustrating a control method of a pulse ablation instrument in accordance with another embodiment of the present application;

FIG. 10 is a flowchart illustrating a control method of a pulse ablation instrument in accordance with yet another embodiment of the present application.

Figures 1, 2:
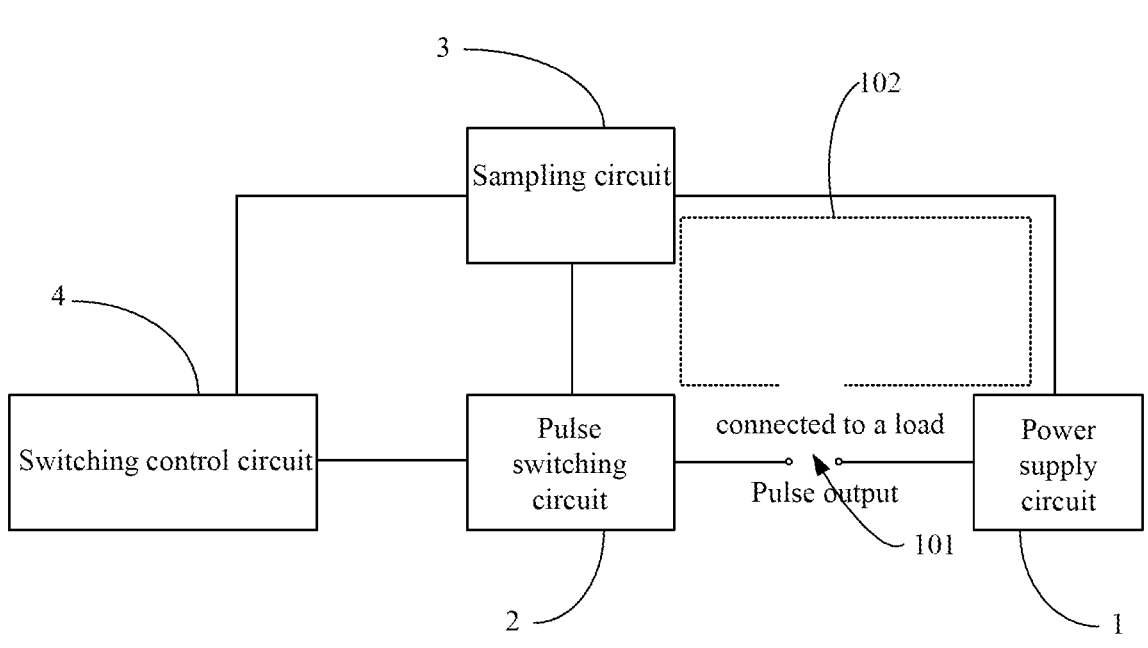
FIG. 1 is a schematic circuit diagram of a pulse ablation instrument in accordance with an embodiment of the present application.
FIG. 2 is a schematic circuit diagram of a pulse ablation instrument in accordance with an embodiment of the present application.

Reference numerals are illustrated as follows:

100, pulse ablation instrument; 1, power supply circuit; 11, first DC power source; 12, second DC power source; 2, pulse switching circuit; 21, first pulse switching component; 211, first terminal of the first pulse switching component; 212, second terminal of the first pulse switching component; 213, control terminal of the first pulse switching component; 22, second pulse switching component; 221, first terminal of the second pulse switching component; 222, second terminal of the second pulse switching component; 223, control terminal of the second pulse switching component; 3, sampling circuit; 31, current transformer; 311, primary winding; 312, secondary winding; 33, voltage dividing circuit; 331, first resistor; 332, second resistor; 4, switching control circuit; 41, pulse regulating circuit; 411, first pulse generator; 412, first pulse width adjustment circuit; 4121, pulse regulating first sub-circuit; 4122, comparator; 4123, flip-flop; 4124, pulse regulating second sub-circuit; 413, second pulse width adjustment circuit; 414, second pulse generator; 43, drive circuit; 431, first drive circuit; 4311, output terminal of the first drive circuit; 432, second drive circuit; 4321, output terminal of the second drive circuit; 5, main control unit; 6, alarm unit; 101, load; 1011, first terminal of the load; 1012, second terminal of the load; 102, power feeding loop

DESCRIPTION OF EMBODIMENTS

The technical solutions in embodiments of the present application will be clearly and fully described below with reference to the accompanying drawings in embodiments of the present application, and it is apparent that the described embodiments are only some, but not all, embodiments of the present application. Based on the embodiments in the present application, all other embodiments obtained by an ordinary one skilled in the art without creative efforts are intended to be within the protection scope of the present application.

In the description of the present application, it needs to be understood that the terms "center", "upper", "lower", "front", "back", "left", "right", "vertical", "horizontal", "top", "bottom", "inner", "outer", etc. indicate an orientation or positional relationship based on the orientation or positional relationship shown in the drawings. It is merely for convenience of description and simplicity of description, and it is not intended to indicate or imply that the device or element referred to must have a particular orientation, be constructed and operate in a particular orientation, and therefore cannot be construed as limiting the present application.

The terms "first", "second", "third" are used for the purpose of description only and are not to be understood as indicating or implying relative importance or implying the number of indicated technical features. Thus, features qualified as "first", "second", and "third" may explicitly or implicitly include one or more such features. In the description of the present application, unless specified otherwise, "plurality" means two or more.

Throughout the descriptions of the present application, unless explicitly specified and defined otherwise, it is to be noted that the terms "in communication", "mounted", "connected", and "connection" should be interpreted in a broad sense, which may be a fixed connection, a detachable connection, or an integral connection; may be a mechanical connection or an electrical connection; a direct connection, an indirect connection through an intermediate medium, or an internal communication between two components. The specific meaning of the above terms in the present application can be understood, on a case-by-case basis, by the ordinary one skilled in the art.

Embodiments of the present application provide a pulse ablation instrument including: a power supply circuit, configured to supply power to a load; a pulse switching circuit, connected to the power supply circuit to regulate a current output by the power supply circuit and flowing to the load; a sampling circuit configured to sample a current flowing through a power feeding loop of the load and obtain a sampling value; a switching control circuit, electrically connected to the sampling circuit and the pulse switching circuit, and configured to output a drive signal which controls an operation of the pulse switching circuit according to the sampling value and reduce a duty cycle of the drive signal to reduce an output current of the power supply circuit when the sampling value is greater than a threshold value.

In some embodiments, the threshold value includes a first threshold value, and when the sampling value is greater than the first threshold value, the switching control circuit reduces the duty cycle of the drive signal cycle by cycle until the sampling value is less than or equal to the first threshold value.

In some embodiments, the threshold value includes a second threshold value, and when the sampling value is greater than the second threshold value, the switching control circuit reduces the duty cycle of the drive signal cycle by cycle until the pulse switching circuit stops working.

In some embodiments, the threshold value includes a first threshold value and/or a second threshold value, when the sampling value is greater than the first threshold value, the switching control circuit reduces the duty cycle of the drive signal cycle by cycle until the sampling value is less than or equal to the first threshold value; and/or when the sampling value is greater than the second threshold value, the switching control circuit reduces the duty cycle of the drive signal cycle by cycle until the pulse switching circuit stops working, wherein the second threshold value is greater than the first threshold value.

In some embodiments, the switching control circuit includes a pulse regulating circuit, configured to generate a pulse signal and adjust a duty cycle of the pulse signal according to the sampling value; and a drive circuit, configured to receive the pulse signal and output the drive signal according to the pulse signal, wherein the duty cycle of the drive signal varies as a function of the duty cycle of the pulse signal.

In some embodiments, the pulse regulating circuit includes: a first pulse generator, configured to generate the pulse signal; a first pulse width adjustment circuit, electrically connected to the first pulse generator, the sampling circuit, and the drive circuit and configured to receive the pulse signal and adjust the duty cycle of the pulse signal according to the sampling value.

In some embodiments, the first pulse width adjustment circuit includes: a pulse regulating first sub-circuit, configured to determine whether the sampling value is greater than the first threshold value according to the sampling value inputted, and reduce the duty cycle of the pulse signal cycle by cycle until the sampling value is less than or equal to the first threshold value when the sampling value is greater than the first threshold value.

In some embodiments, the first pulse width adjustment circuit further includes: a comparator, wherein a non-inverting input terminal of the comparator receives the sampling value, an inverting input terminal of the comparator receives the second threshold value, when the sampling value is greater than the second threshold value, the comparator outputs a trigger level; a flip-flop, configured to receive the trigger level and output a control signal; and a pulse regulating second sub-circuit, configured to reduce the duty cycle of the pulse signal cycle by cycle according to the control signal until the duty cycle of the pulse signal falls to zero In some embodiments, the pulse ablation instrument further includes a main control unit, the main control unit controls an alarm unit to alarm when the sampling value is greater than the second threshold value; the main control unit is further configured to send a reset signal to the flip-flop according to an external reset instruction to cause the flip-flop to reset and stop outputting the control signal.

In some embodiments, the pulse regulating circuit includes: a second pulse width adjustment circuit, electrically connected to the sampling circuit and configured to generate a duty cycle adjustment signal according to the sampling value; and a second pulse generator, electrically connected to the second pulse width adjustment circuit and the drive circuit and configured to generate a pulse signal according to the duty cycle adjustment signal, wherein the duty cycle of the pulse signal is adjusted by the duty cycle adjustment signal.

In some embodiments, the power supply circuit includes a first DC power source; the pulse switching circuit includes a first pulse switching component; a first terminal of the first pulse switching component is connected to a positive pole of the first DC power source, a second terminal of the first pulse switching component is connected to a first terminal of the load, a second terminal of the load is connected to a negative pole of the first DC power source, and a control terminal of the first pulse switching component is connected to an output terminal of the drive circuit.

In some embodiments, the power supply circuit further includes a second DC power source, a positive pole of the second DC power source is connected to the second terminal of the load and the negative pole of the first DC power source; the pulse switching circuit further includes a second pulse switching component, a first terminal of the second pulse switching component is connected to the first terminal of the load, a second terminal of the second pulse switching component is connected to the negative pole of the second DC power source, and a control terminal of the second pulse switching component is connected to the drive circuit. The pulse regulating circuit is configured to generate a first pulse signal and a second pulse signal, the drive circuit includes a first drive circuit and a second drive circuit; an output terminal of the first drive circuit is connected to the control terminal of the first pulse switching component, the first drive circuit is configured to receive the first pulse signal and output a first drive signal to drive an operation of the first pulse switching component; an output terminal of the second drive circuit is connected to the control terminal of the second pulse switching component, the second drive circuit is configured to receive the second pulse signal and output a second drive signal to drive an operation of the second pulse switching component.

In some embodiments, both of the first pulse switching component and the second pulse switching component are IGBT transistors.

In some embodiments, both of the first pulse switching component and the second pulse switching component are MOS transistors.

In some embodiments, the sampling circuit includes one or more current transformers, the current transformer includes a primary winding and a secondary winding; the primary winding is connected in series with the power feeding loop of the load, and the secondary winding is electrically connected with the switching control circuit, the secondary winding is configured to output the sampling value.

In some embodiments, the sampling circuit further includes a voltage dividing circuit, the voltage dividing circuit includes a first resistor and a second resistor which are connected in series between an output terminal of the secondary winding of the current transformer and a ground terminal of the secondary winding of the current transformer, a connection point where the first resistor and the second resistor are connected together outputs the sampling value.

Embodiments of the present application also provide a control method of a pulse ablation instrument, including steps of: sampling a current flowing through a power feeding loop of a load and obtaining a sampling value; and reducing a duty cycle of a drive signal which controls an operation of a pulse switching circuit to reduce a current output to the load when the sampling value is greater than a threshold value.

In some embodiments, the threshold value includes a first threshold value, the step of reducing a duty cycle of a drive signal which controls an operation of a pulse switching circuit when the sampling value is greater than a threshold value includes a step of: reducing the duty cycle of the drive signal cycle by cycle until the sampling value is less than or equal to the first threshold value when the sampling value is greater than the first threshold value.

In some implementations, the threshold value includes a second threshold value, the step of reducing a duty cycle of a drive signal which controls an operation of a pulse switching circuit when the sampling value is greater than a threshold value includes a step of: reducing the duty cycle of the drive signal cycle by cycle until the pulse switching circuit stops working when the sampling value is greater than the second threshold value.

In some embodiments, the threshold value includes a first threshold value and/or a second threshold value, the step of reducing the duty cycle of the drive signal which controls an operation of the pulse switching circuit when the sampling value is greater than the threshold value includes steps of: reducing the duty cycle of the drive signal cycle by cycle until the sampling value is less than or equal to the first threshold value when the sampling value is greater than the first threshold value; and/or reducing the duty cycle of the drive signal cycle by cycle until the pulse switching circuit stops working when the sampling value is greater than the second threshold value, wherein the second threshold value is greater than the first threshold value.

The present application also provides an electronic device including: a processor; and a memory configured to store executable instructions of the processor; wherein the processor is configured to execute the executable instructions to perform the control method of a pulse ablation instrument of the above embodiments.

The present application also provides a control apparatus of a pulse ablation instrument including: a sampling module, configured to sample a current flowing through a power feeding loop of a load and obtain a sampling value; and a current control module, configured to reduce a duty cycle of a drive signal which controls an operation of a pulse switching circuit to reduce a current output to the load when the sampling value is greater than a threshold value.

In some embodiments, the threshold value includes a first threshold value and/or a second threshold value, the current control module includes: a first duty cycle adjustment unit, configured to reduce the duty cycle of the drive signal cycle by cycle until the sampling value is less than or equal to the first threshold value when the sampling value is greater than the first threshold value; and/or a second duty cycle adjustment unit, configured to reduce the duty cycle of the drive signal cycle by cycle until the pulse switching circuit stops working when the sampling value is greater than the second threshold value, wherein the second threshold value is greater than the first threshold value.

The present application also provides a computer readable medium having stored a computer program thereon which, when executed by a processor, implements a control method of a pulse ablation instrument including: sampling a current flowing through a power feeding loop of a load and obtaining a sampling value; and reducing a duty cycle of a drive signal which controls an operation of a pulse switching circuit to reduce a current output to the load when the sampling value is greater than a threshold value.

In some embodiments, the threshold value includes a first threshold value and/or a second threshold value, the step of reducing a duty cycle of a drive signal which controls an operation of a pulse switching circuit when the sampling value is greater than a threshold value includes steps of: reducing the duty cycle of the drive signal cycle by cycle until the sampling value is less than or equal to the first threshold value when the sampling value is greater than the first threshold value; and/or reducing the duty cycle of the drive signal cycle by cycle until the pulse switching circuit stops working when the sampling value is greater than the second threshold value, wherein the second threshold value is greater than the first threshold value.

The pulse ablation instrument and control method, control apparatus thereof, electronic device, and media in accordance with embodiments of the present invention sample the current flowing through the load and the power feeding loop of the load, and reduce the duty cycle of the pulse signal to reduce the current output to the load when the sampling value is greater than the threshold value, therefore, when the current flowing through the load and the power feeding loop of the load is excessive, the current flowing through the load and the power feeding loop of the load is reduced in real time, thereby protecting the switching components of the pulse switching circuit in the power feeding loop of the load, and preventing the switching components of the pulse switching circuit from being damaged by sustained large current shocks. Furthermore, the pulse ablation instrument and control method, control apparatus, electronic device, and media thereof in accordance with embodiments of the present application can also prevent the load from being subjected to large current for long periods of time, thereby avoiding harm to the load.

In the related art, the internal circuit of the pulse ablation instrument and the load is protected by connecting a protection resistor in series with the power feeding loop of the load in the pulse ablation instrument. However, this solution suffers from the following drawbacks that: when the load impedance of the pulse ablation instrument is low, the protection resistor connected in series with the pulse output circuit will divide the output pulse voltage, resulting in a large difference between the pulse voltage value on the load and the DC high voltage, which fails to reach the pulse voltage level required by the electroporation technique, such that the ablation effect is reduced. It is also a problem to be solved that how to prevent switching components and the like of the internal circuit of the pulse ablation instrument from being damaged by sustained large current shocks while not reducing the output voltage across the load.

Referring to FIG. 1, a pulse ablation instrument 100 in accordance with an embodiment of the present application includes a power supply circuit 1, a pulse switching circuit 2, a sampling circuit 3, and a switching control circuit 4.

The power supply circuit 1 is configured to supply power to the load 101. The pulse switching circuit 2 is connected to the power supply circuit 1 to regulate the current output by the power supply circuit 1 and flowing to the load 101. The sampling circuit 3 is configured to sample the current flowing through the power feeding loop 102 of the load and obtain a sampling value. The switching control circuit 4 is electrically connected to the sampling circuit 3 and the pulse switching circuit 2, and is configured to output a drive signal which controls an operation of the pulse switching circuit 2 according to the sampling value, and reduce the duty cycle of the drive signal to reduce the output current of the power supply circuit 1 when the sampling value is greater than a threshold value.

The switching components of a pulse output circuit operate in high voltage and high current operating conditions, are vulnerable to high current shocks and thus are damaged when the load is short-circuited or the load current is excessive. It is therefore a problem to be solved how to prevent the switching components from being damaged by large current shocks when the load is short-circuited or the load current is excessive. The pulse ablation instrument according to an embodiment of the present application is provided with the sampling circuit to sample the current flowing through the load and the power feeding loop of the load, when the sampling value is greater than the threshold value, the switching control circuit is configured to reduce the duty cycle of the pulse signal to reduce an output current of the power supply circuit, such that the current flowing through the load and the pulse switching components is reduced in real time when the current flowing through the load and the power feeding loop of the load is excessive, thereby protecting the switching components in the pulse switching circuit, and preventing the switching components from being damaged by sustained large current shocks. Moreover, the present application may also prevent the load from being subjected to large currents for long periods of time, thereby avoiding harm to the load.

The pulse ablation instrument controls the power supply circuit 1 to supply power directly to the load through the pulse switching circuit 2, which prevents the problem in the prior art that the protective resistor or the like connected in series with the power supply circuit from dividing the output pulse voltage and resulting in a large difference between the pulse voltage on the load and the DC high voltage, such that the ablation effect is improved.

Further descriptions are provided below in conjunction with the accompany drawings.

Figure 3:
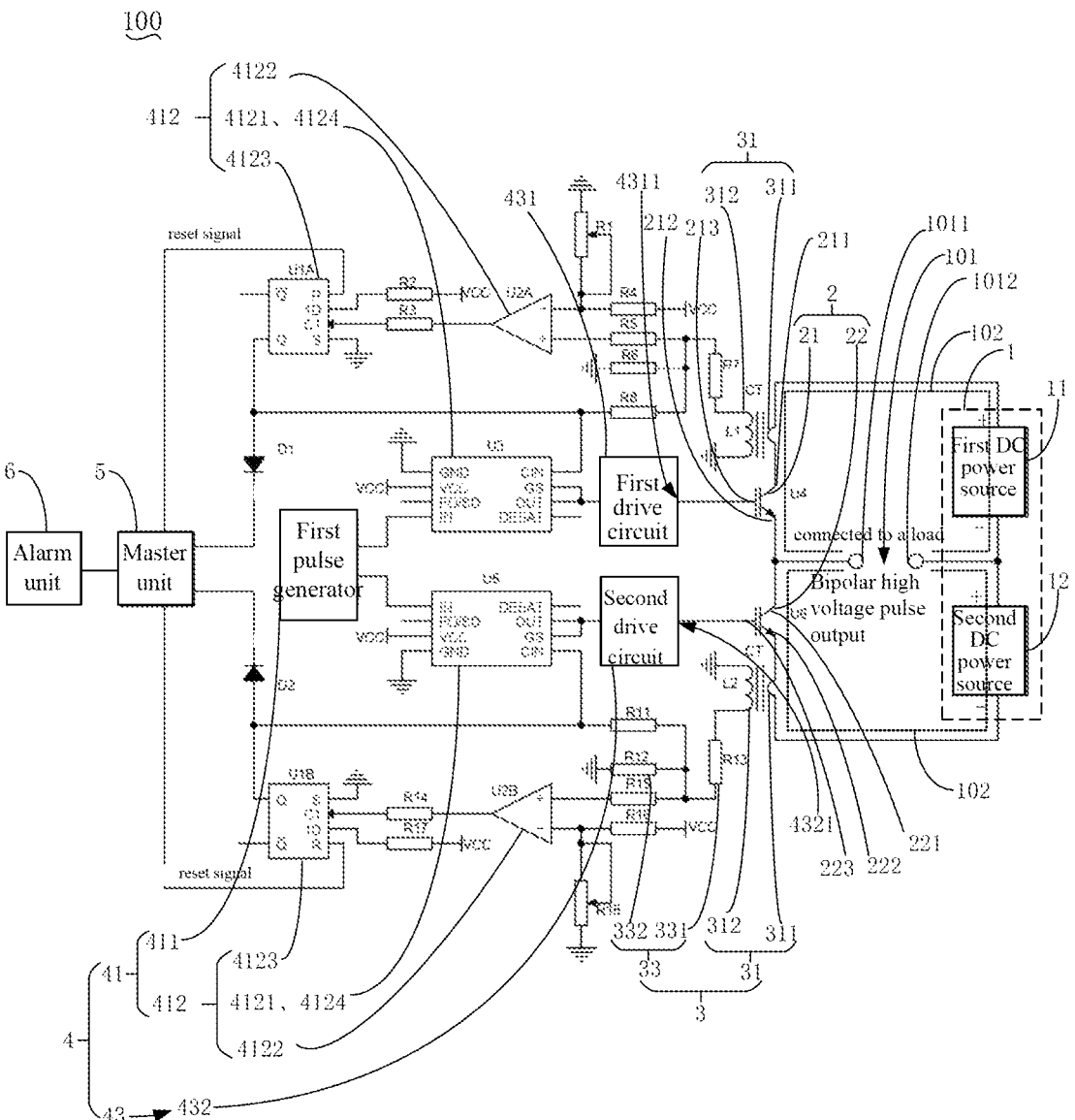
FIG. 3 is a circuit diagram of a pulse ablation instrument in accordance with an embodiment of the present application.

Referring to FIGS. 2 and 3, the pulse ablation instrument 100 includes a power supply circuit 1, a pulse switching circuit 2, a sampling circuit 3, and a switching control circuit 4. The power supply circuit 1 is configured to supply power to a load. The load may be biological tissue or the like. The power supply circuit 1 includes a direct current (DC) power supply. The DC power supply may be implemented by converting the mains power to a DC power through an inverter circuit and a rectifier filter circuit and storing the DC power in an energy storage capacitor. The power supply circuit may be formed by one or more high voltage DC power supplies, which may output high voltage pulses to the load. The voltage of the high voltage pulse reaches the pulse voltage level required by the electroporation technique, which can achieve better ablation effect. The high voltage DC power supply in the power supply circuit can output high voltage power in the range of, but not limited to, 500 V to 4000 V, for example, the high voltage DC power supply may be used to output the high voltage power at 500 V, 1000 V, 2500 V, 3000 V, 4000 V, and different output voltages of the high voltage DC power supply may be used for different load types to enhance ablation effect and facilitate protection of the load and internal circuit of the pulse ablation instrument. The pulse switching circuit 2 is connected to the power supply circuit 1 to regulate the current output by the power supply circuit 1 and flowing to the load 101. The power supply circuit 1 and the pulse switching circuit 2 form the power feeding loop 102 of the load 101.

In some embodiments, the power supply circuit 1 and pulse switching circuit 2 are configured to output a unipolar pulse current to the load. The power supply circuit 1 includes a first DC power supply 11; the pulse switching circuit 2 includes a first pulse switching component 21. A first terminal 211 of the first pulse switching component 21 is connected to the positive pole of the first DC power source 11, a second terminal 212 of the first pulse switching component 21 is connected to a first terminal 1011 of the load 101, a second terminal 1012 of the load 101 is connected to the negative pole of the first DC power source 11, and a control terminal 213 of the first pulse switching component 21 is connected to an output terminal of the drive circuit 43, specifically, the control terminal 213 of the first pulse switching component 21 is connected to the output terminal 4311 of the first drive circuit 431. The first drive signal output by the first drive circuit 431 controls the first pulse switching component 21 to turn on or turn off, such that the power supply circuit 1 outputs unipolar pulses to the load. As a result, the pulse ablation instrument 100 can output a unipolar pulse current to the load with a simple circuit construction, it is advantageous for improving the stability of the operation of the circuit of the pulse ablation instrument 100.

In other embodiments, the power supply circuit 1 and the pulse switching circuit 2 are configured to output a bipolar pulse current to the load 101. The power supply circuit 1 includes a first DC power supply 11 and a second DC power supply 12; the pulse switching circuit 2 includes a first pulse switching component 21 and a second pulse switching component 22. The first terminal 211 of the first pulse switching component 21 is connected to the positive pole of the first DC power supply 11, the second terminal 212 of the first pulse switching component 21 is connected to the first terminal 1011 of the load 101, the second terminal 1012 of the load 101 is connected to the negative pole of the first DC power supply 11, and the control terminal 213 of the first pulse switching component 21 is connected to the output terminal 4311 of the first drive circuit 431. The positive pole of the second DC power source 12 is connected to the second terminal 1012 of the load 101 and the negative pole of the first DC power source 11, the first terminal 221 of the second pulse switching component 22 is connected to the first terminal 1011 of the load 101, the second terminal 222 of the second pulse switching component 22 is connected to the negative pole of the second DC power supply 12 and the control terminal 223 of the second pulse switching component 22 is connected to the drive circuit 43, specifically, the control terminal 223 of the second pulse switching component 22 is connected to the output terminal 4321 of the second drive circuit 432. The first drive signal output by the first drive circuit 431 controls the first pulse switching component 21 to turn on or turn off, the second drive signal output by the second drive circuit 432 controls the second pulse switching component 22 to turn on or turn off, such that the first pulse switching component 21 and the second pulse switching component 22 are alternately switched on and alternately switched off, so that the power supply circuit 1 outputs bipolar pulses to the load. As such, the pulse ablation instrument 100 may output a bipolar pulse current to the load. The bipolar pulse current ablation provided by the present embodiment may result in a more uniform electric field distribution, which may reduce muscle contraction issues during the use of the pulse ablation instrument, which in turn makes the pulse ablation instrument have better ablation effect while improving the safety of the ablation process on biological tissue.

In some embodiments, both of the first pulse switching component 21 and the second pulse switching component 22 are IGBT transistors. Alternatively, both of the first pulse switching component 21 and the second pulse switching component 22 are MOS transistors. Therefore, the drive signal is able to drive the first pulse switching component 21 through the control terminal 213 thereof and drive the second pulse switching component 22 through the control terminal 223 thereof, to control the current flowing through the load 101 and the pulse switching device 2.

Referring to FIGS. 2 and 3, the sampling circuit 3 is configured to sample the current flowing through the power feeding loop 102 of the load 101 and obtain a sampling value.

The sampling circuit 3 includes one or more current transformers 31. The current transformer 31 may have a transformation ratio of, but not limited to, 1:50, 1:80, 1:100 or 1:200, such that even when the sampling current i.e., the current flowing through the power feeding loop 102 of the load 101 is large, the induced sampling value is not too high, which advantageously avoids damage to the sampling circuit when the sampling current is excessive, and advantageously maintains stable operation of the circuits of the pulse ablation instrument. The current transformer 31 includes a primary winding 311 and a secondary winding 312. The primary winding 311 is connected in series with the power feeding loop 102 of the load 101, and the secondary winding 312 is electrically connected to the switching control circuit 4. The secondary winding 312 is configured to output the sampling value. Sampling the current of the power feeding loop 102 of the load 101 by means of the current transformer 31 can effectively isolate the high voltage circuit on the load side from the lower voltage circuit on the sampling circuit side, which prevents the high voltage circuit on the load side from damaging the sampling circuit 3.

Further, the sampling circuit 3 also includes a voltage dividing circuit 33, the voltage dividing circuit 33 includes a first resistor 331 and a second resistor 332 which are connected in series between the output terminal of the secondary winding 312 of the current transformer 31 and a ground terminal, a connection point where the first resistor 331 and the second resistor 332 are connected together outputs the sampling value. When the sampling circuit 3 includes a plurality of current transformers 31, the sampling circuit 3 may include a plurality of voltage dividing circuits 33 corresponding to the plurality of current transformers 31. For example, as shown in the embodiment of FIG. 3, the sampling circuit 3 includes two current transformers 31 and voltage dividing circuits 33 each of which corresponds to one current transformer 31. The current transformer L1 corresponds to the voltage dividing circuit 33 formed by a first resistor R7 and a second resistor R6; the current transformer L2 corresponds to the voltage dividing circuit 33 formed by a first resistor R13 and a second resistor R12. Compared with directly taking the induced voltage induced by the current transformer 31 as a sampling value, the induced voltage induced by the current transformer 31 is divided by the voltage dividing circuit 33, and a voltage value output from a point connecting the first resistor 331 and the second resistor 332 is taken as the sampling value, which is advantageous to reduce the voltage of the sampling value output by the sampling circuit and thereby protecting the internal circuit of the pulse ablation instrument.

With continued reference to FIG. 3, the sampling value output by the sampling circuit 3 may further be output to the switching control circuit 4 through a current limiting resistor, such that excessive current flows into the switching control circuit 4 may be avoided, thereby advantageously protecting the internal circuit of the switching control circuit 4. In particular, the sampling value output by the sampling circuit 3 is output to the switching control circuit 4 through current limiting resistors R8 and R11, and the sampling value output by the sampling circuit 3 is output to the switching control circuit 4 through current limiting resistors R7 and R15.

The switching control circuit 4 is electrically connected to the sampling circuit 3 and the pulse switching circuit 2, and is configured to output a drive signal which controls an operation of the pulse switching circuit 2 according to the sampling value and reduce a duty cycle of the drive signal when the sampling value is greater than a threshold value, to reduce the output current of the power supply circuit, thereby protecting the pulse switching circuit 2 and preventing the pulse switching circuit 2 from being damaged by excessive current; at the same time, it can also prevent the load from being subjected to large current for long periods of time, so that hazards to the load can be avoided.

In some embodiments, the threshold value includes a first threshold value, the first threshold value may correspond to a threshold that the sampling value exceeds when the load current is excessive. When the sampling value is greater than the first threshold value, the switching control circuit 4 reduces the duty cycle of the drive signal cycle by cycle until the sampling value is less than or equal to the first threshold value. Therefore, when the current flowing through the load and the pulsing switch circuit is excessive, the switching control circuit 4 achieves reducing the current flowing through the load and the pulse switching circuit, i.e., reducing the output current of the power supply circuit, until the current flowing through the load and the pulse switching circuit returns to normal, and achieves over-current protection of the circuit in which the load and the pulse switching circuit are located, i.e., over-current protection of the power feeding loop of the load.

In some embodiments, the threshold value includes a second threshold value that is greater than the first threshold value, and the second threshold value may correspond to a threshold that the sampling value exceeds when the load is short-circuited. When the sampling value is greater than the second threshold value, the switching control circuit 4 reduces the duty cycle of the drive signal cycle by cycle until the pulse switching circuit stops working. Therefore, when the load is short-circuited, the switching control circuit 4 achieves reducing the duty cycle of the drive signal cycle by cycle until the pulse switching circuit stops working, and achieves gradually reducing the output current of the power supply circuit, turning off the pulse switching component in a "soft landing" manner, which may prevent large transient change in current from resulting in induced voltage spikes, thereby advantageously improving circuit safety of the process of turning off the pulse switching circuit when the load is short-circuited, and achieving short-circuit protection of the load and the circuit in which the pulse switching circuit is located, i.e., short-circuit protection of the power feeding loop of the load.

In some implementations, the threshold value includes a first threshold value and/or a second threshold value. When the sampling value is greater than the first threshold value, the switching control circuit 4 reduces the duty cycle of the drive signal cycle by cycle until the sampling value is less than or equal to the first threshold value. When the sampling value is greater than the second threshold value, the switching control circuit 4 reduces the duty cycle of the drive signal cycle by cycle until the pulse switching circuit stops working, wherein the second threshold value is greater than the first threshold value. In particular examples, the first threshold value may be adjusted as appropriate and may include, but is not limited to, values ranging between 430 mV and 550 mV, such as 430 mV, 440 mV, 450 mV, 460 mV, 470 mV, 480 mV, 490 mV, 500 mV, 510 mV, 520 mV, 530 mV, 540 mV, 550 mV, or the like. The second threshold value may be adjusted as appropriate and may include, but is not limited to, values ranging between 1.0 V and 2.0 V, such as 1.0 V, 1.1 V, 1.2 V, 1.3 V, 1.4 V, 1.5 V, 1.6 V, 1.7 V, 1.8 V, 1.9 V, 2.0 V, and the like. Therefore, the switching control circuit 4 simultaneously achieves over-current protection and short-circuit protection of the load and the circuit in which the pulse switching circuit is located. In addition, the second threshold value is greater than the first threshold value, which can distinguish the first threshold value that the sampling value needs to reach when the over-current protection is triggered and the second threshold value that the sampling value needs to reach when the short-circuit protection is triggered, so that both over-current protection and short-circuit protection of the load and the circuit in which the pulse switching circuit is located can be implemented simultaneously in the same control logic.

In particular, with continued reference to FIGS. 2 and 3, the switching control circuit 4 includes a pulse regulating circuit 41 and a drive circuit 43. The pulse regulating circuit 41 is configured to generate a pulse signal and to adjust the duty cycle of the pulse signal according to the sampling value. The drive circuit 43 is configured to receive the pulse signal and output a drive signal according to the pulse signal, the duty cycle of the drive signal varies as a function of the duty cycle of the pulse signal.

The pulse regulating circuit 41 is configured to generate a first pulse signal and a second pulse signal. The first pulse signal and the second pulse signal may be a pair of pulse signals having the same frequency and duty cycle and 180 degrees out of phase.

The drive circuit 43 includes a first drive circuit 431 and a second drive circuit 432.

The output terminal 4311 of the first drive circuit 431 is connected to the control terminal 213 of the first pulse switching component 21. The first drive circuit is configured to receive the first pulse signal and output a first drive signal to drive an operation of the first pulse switching component 21.

The output terminal 4321 of the second drive circuit 432 is connected to the control terminal 223 of the second pulse switching component 22. The second drive circuit 432 is configured to receive the second pulse signal and output the second drive signal to drive an operation of the second pulse switching component 22.

In some embodiments, referring to FIG. 3, the pulse regulating circuit 41 includes a first pulse generator 411 and a first pulse width adjustment circuit 412. The first pulse generator 411 is configured to generate a pulse signal. In particular, the first pulse generator 411 may be configured to output a pulse signal with a fixed duty cycle. The first pulse generator 411 may generate a pulse signal with a fixed duty cycle when the power supply circuit 1 and the pulse switching circuit 2 are used to output a unipolar pulse current to the load. The first pulse generator 411 may be a complementary symmetric PWM waveform generator capable of simultaneously generating and outputting a pair of pulse signals with the same frequency and duty cycle and 180 degrees out of phase, when the power supply circuit 1 and the pulse switching circuit 2 are used to output a bipolar pulse current to the load 101. The first pulse width adjustment circuit 412 is electrically connected to the first pulse generator 411, the sampling circuit 3 and the drive circuit 43 and is configured to receive the pulse signal and adjust the duty cycle of the pulse signal according to the sampling value. The first pulse width adjustment circuit 412 includes a pulse regulating first sub-circuit 4121. As shown in FIG. 3, the pulse regulating first sub-circuit 4121, i.e., the pulse regulating first sub-circuit U3 and the pulse regulating first sub-circuit U5 shown in FIG. 3, receives the sampling value through the CIN pin, and determines, based on the sampling value inputted, whether the sampling value is greater than the first threshold value. The first threshold value may be adjusted according to practical circumstances and is applicable in a wider range. However, in some embodiments, the first pulse generator 411 may be configured to output a pulse signal with an unfixed duty cycle.

The pulse regulating first sub-circuit 4121 reduces the duty cycle of the pulse signal cycle by cycle until the sampling value is less than or equal to the first threshold value when the sampling value is greater than the first threshold value. That is, when the sampling value received by the CIN pin of the pulse regulating first sub-circuit 4121 is greater than the first threshold value, the pulse regulating first sub-circuit 4121 reduces the duty cycle of the pulse signal and outputs the pulse signal with a reduced duty cycle. when the next cycle of the pulse signal comes, if the sampling value received by the CIN pin is still greater than the first threshold value, the duty cycle of the current cycle of the pulse signal is reduced further and then the pulse signal is output, the step is repeated until the sampling value received by the CIN pin is less than or equal to the first threshold value. A pulse-by-pulse width adjustment circuit may be integrated into the pulse regulating first sub-circuit, which may achieve reducing the duty cycle of the pulse signal cycle by cycle. In some embodiments, reducing the duty cycle of the outputted pulse signal cycle by cycle maybe performed by, but is not limited to, the following two ways: (1) if an original duty cycle is 30%, reducing as a duty cycle of 29%, 28%, 27%, 26% . . . ; (2) scaling down in proportion to the duty cycle, for example, if the original duty cycle is 30%, multiplying the duty cycle by a factor less than 1 per cycle to achieve a reduction of the duty cycle, for example, 30%, 30%*0.9, 30%*0.9*0.9, 30%*0.9*0.9* 0.9 . . . or selecting other larger or smaller proportional reduction means depending on the actual situation. Thus, the switching control circuit 4 may achieve over-current protection of the load and the circuit in which the pulse switching circuit is located through the first pulse width adjustment circuit 412.

Figures 4, 5:
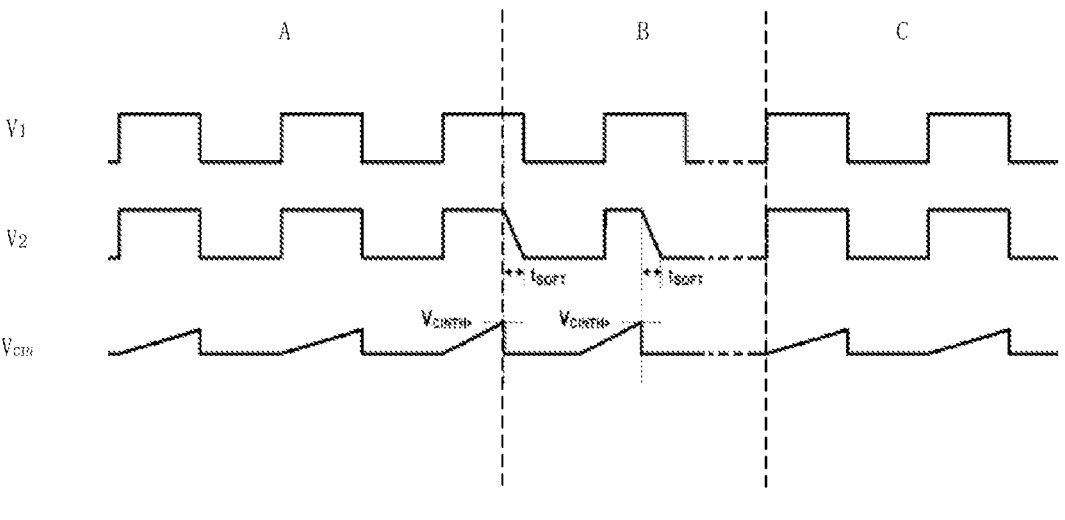
FIG. 4 is a schematic diagram illustrating a pulse waveform and a waveform of sampling values as functions of time in accordance with an embodiment of the present application.
FIG. 5 is a schematic circuit diagram of a pulse ablation instrument in accordance with another embodiment of the present application.

Referring to FIG. 4, region A of FIG. 4 shows the pulse signal V1 generated by the first pulse generator 411, the pulse signal V2 obtained by adjusting the duty cycle of the pulse signal V1 according to the sampling value via the first pulse width adjustment circuit 412, and the signal $V_{CIN}$ received by the CIN pin of the pulse regulating first sub-circuit U3 or the pulse regulating first sub-circuit U5, i.e., the signal that the sampling value varies with time, when the current of the power feeding loop 102 of the load 101 is in the normal range i.e., $V_{CIN}$ is less than the first threshold value $V_{CINTH+}$ (which is referred to as the same hereinafter). The $V_{CINTH+}$ is the first threshold value. In the region A, when the current of the power feeding loop 102 of the load 101 is in the normal range, the first pulse width adjustment circuit 412 outputs the pulse signal V2 having a duty cycle consistent with the pulse signal V1. When an overcurrent of the current of the power feeding loop 102 of the load 101 i.e., the situation that the signal $V_{CIN}$ received by the pulse regulating first sub-circuit reaches or exceeds the first threshold value $V_{CINTH+}$ (which is referred to as the same hereinafter) occurs, as shown in region B of FIG. 4, the pulse regulating first sub-circuit 4121 reduces the duty cycle of the outputted pulse signal V2 cycle by cycle until $V_{CIN}$ is less than the first threshold value $V_{CINTH+}$, and maintains the current duty cycle of the outputted pulse signal V2 unchanged until the overcurrent condition disappears or the pulse ablation instrument is reset. As shown in region C of FIG. 4, when receiving an external reset instruction, the first pulse width adjustment circuit 412 resumes normal output, i.e., outputs the pulse signal V2 with a duty cycle consistent with the pulse signal V1. If the condition that $V_{CIN}$ reaches or exceeds the first threshold value $V_{CINTH+}$ no longer occurs at this point, the first pulse width adjustment circuit 412 continues to output the pulse signal V2 with a duty cycle consistent with the pulse signal V1.

In other embodiments of the present application, the first pulse width adjustment circuit 412 outputs the pulse signal V2 having a duty cycle that is maintained at a fixed proportional relationship to the duty cycle of the pulse signal V1 when the current of the power feeding loop 102 of the load 101 is in a normal range, which may facilitate regulation of the output pulse signal V2, to produce the pulse signal V2 applicable to the current gear of the pulse ablation instrument. For example, the first pulse width adjustment circuit 412 outputs the pulse signal V2 having a duty cycle that is 0.4, 0.5, 0.6, 0.7, 0.8, 1.2, 1.3, 1.4, 1.5, or 1.6 times of the duty cycle of the pulse signal V1.

Further, the first pulse width adjustment circuit 412 may further include a comparator 4122, a flip flop 4123, and a pulse regulating second sub-circuit 4124. The non-inverting input terminal of the comparator 4122 receives the sampling value and the inverting input terminal of the comparator 4122 receives the second threshold value. When the sampling value is greater than the second threshold value, the comparator 4122 outputs a trigger level. The second threshold value of the comparator may be a reference voltage. The reference voltage may be output from a connecting point between a fixed resistor and an adjustable resistor which are connected in series. One end of the fixed resistor is connected to the adjustable resistor and the other end of the fixed resistor is connected to the power supply VCC. One end of the adjustable resistor is connected to the fixed resistor and the other end of the adjustable resistor is grounded. In FIG. 3, the adjustable resistors are R1 and R18, the fixed resistors are R4 and R16, by adjusting R1 and R18, the second threshold value may be adjusted and modified according to actual situation, for a wider range of application. The flip-flop 4123 is configured to receive the trigger level and output a control signal to the CIN pin of the pulse regulating second sub-circuit 4124.

In some embodiments, as shown in FIG. 3, the pulse regulating first sub-circuit 4121 and the pulse regulating second sub-circuit 4124 are implemented in the same chip, then the CIN pin of the pulse regulating first sub-circuit 4121 and the CIN pin of the pulse regulating second sub-circuit 4124 are the same pin, and thus over-current protection and short-circuit protection of the circuit where the load and the pulse switch circuit are located are achieved by the first pulse width adjustment circuit 412 via the same CIN pin.

Specifically, the flip-flop 4123 may be a D flip-flop, an RS flip-flop, or the like. In the embodiment, the flip-flop 4123 shown in FIG. 3 is a D flip-flop. When the flip-flop 4123 is in the other form, such as an RS flip-flop, corresponding modifications to the support circuit of the flip-flop 4123 in the embodiment presented in FIG. 3 are needed to comply with the level control logic. The pulse regulating second sub-circuit 4124 is configured to reduce the duty cycle of the pulse signal cycle by cycle according to the control signal until the duty cycle of the pulse signal falls to zero. That is, when the pulse regulating second sub-circuit 4124 receives the trigger level, i.e., the sampling value, output by the comparator 4122 which is greater than the second threshold value, the pulse regulating second sub-circuit 4124 reduces the duty cycle of the pulse signal and outputs the pulse signal with the reduced duty cycle, when the next cycle of the pulse signal comes, the pulse regulating second sub-circuit 4124 further reduces the duty cycle of the current period of the pulse signal and output the pulse signal, and the step is repeated until the duty cycle of the current period of the pulse signal drops to zero, to slowly switch off the pulse switching circuit 2 to achieve a power outage "soft landing", thereby achieving protection of the pulse ablation instrument and the load.

Further, when the pulse regulating second sub-circuit 4124 receives the trigger level, i.e., the sampling value, output by the comparator 4122 which is greater than the second threshold value, the pulse regulating second sub-circuit 4124 will reduce the duty cycle of the pulse signal at a faster rate than that when the sample value received by the pulse regulating first sub-circuit 4121 is greater than the first threshold value, which may improve circuit safety of the pulse ablation instrument in the event of a short circuit in the power feeding loop of the load. Thus, the switching control circuit 4 may achieve short circuit protection of the load and the circuit in which the pulse switching circuit is located through the first pulse width adjustment circuit 412.

The pulse regulating first sub-circuit 4121 and the pulse regulating second sub-circuit 4124 may be implemented by the same integrated circuit. Alternatively, the pulse regulating first sub-circuit 4121 and the pulse regulating second sub-circuit 4124 may be implemented by two identical integrated circuits. Alternatively, the pulse regulating first sub-circuit 4121 and the pulse regulating second sub-circuit 4124 may be implemented by two different integrated circuits, the two different integrated circuits may differently reduce the duty cycle of the pulse signal cycle by cycle, and the integrated circuit corresponding to the pulse regulating second sub-circuit 4124 reduces the duty cycle of the pulse signal cycle by cycle at a faster rate than that at which the integrated circuit corresponding to the pulse regulating first sub-circuit 4121 reduces the duty cycle of the pulse signal cycle by cycle.

The pulse ablation instrument 100 may also include a main control unit 5 and an alarm unit 6. Referring to FIG. 3, the flip-flop 4123 also sends the control signal to the main control unit 5 through diodes D1 and diodes D2 when the sampling value is greater than the second threshold value, the main control unit 5 then controls the alarm unit 6 to raise an alarm, which may be in the form of an acousto-optic alarm. The main control unit 5 may also send a reset signal to the flip-flop 4123 according to an external reset instruction to make the flip-flop 4123 reset and stop outputting the control signal. The control signal is sent to the main control unit 5 through the diode, which prevent the control signal from being influenced by the internal voltage of the main control unit 5, and thus the control signal can be prevented from being affected, thereby avoiding affecting the process of reducing the duty cycle of the pulse signal cycle by cycle until the duty cycle of the pulse signal falls to zero by the pulse regulating second sub-circuit 4124, and advantageously improving the functional operational stability of the short circuit protection of the pulse regulating second sub-circuit. In a specific application scenario, when a short circuit condition occurs, the sampling value acquired by the sampling circuit 3 is greater than the second threshold value, which will cause the flip-flop 4123 to send the control signal to the main control unit 5 through diodes D1 and D2, such that the main control unit 5 controls the alarm unit 6 to alarm. When the operator hears the alarm sound or see the alarm light, the operator will check whether there is a short circuit condition of the pulse ablation instrument 100 and the load 101. When the short circuit fault is precluded, the operator may then press the reset key of the pulse ablation instrument 100, or otherwise issue an external reset command to the main control unit 5, so that the flip-flop 4123 may be reset to allow the internal circuit of the pulse ablation instrument to re-function properly.

In other embodiments, referring to FIG. 5, the pulse regulating circuit 41 includes a second pulse width adjustment circuit 413 and a second pulse generator 414. The second pulse width adjustment circuit 413 is electrically connected to the sampling circuit 3 and is configured to generate a duty cycle adjustment signal according to the sampling values. The second pulse generator 414 is electrically connected to the second pulse width adjustment circuit 413 and the drive circuit 43 and is configured to generate a pulse signal according to the duty cycle adjustment signal, the duty cycle of the pulse signal is adjusted by the duty cycle adjustment signal, the duty cycle adjustment signal directly controls the second pulse generator 414 to generate a duty cycle controlled pulse signal.

The second pulse width adjustment circuit 413 may include a microprocessor. The microprocessor of the second pulse width adjustment circuit 413 may receive the sampling value and output the duty cycle adjustment signal according to the sampling value through internal processing of the microprocessor. Specifically, when the sampling value is greater than the first threshold value, the second pulse width adjustment circuit 413 may output a duty cycle adjustment signal to reduce the duty cycle of the pulse signal output by the second pulse generator 414 cycle by cycle, thereby reducing the duty cycle of the drive signal output by the drive circuit 43 cycle by cycle until the sampling value is less than or equal to the first threshold value. When the sampling value is greater than the second threshold value, the second pulse width adjustment circuit 413 may output the duty cycle adjustment signal to reduce the duty cycle of the pulse signal cycle by cycle, thereby reducing the duty cycle of the drive signal cycle by cycle until the pulse switching circuit stops working. The second threshold value is greater than the first threshold value. Therefore, the switching control circuit 4 can simultaneously achieve over-current protection and short-circuit protection for the load and the circuit in which the pulse switching circuit is located through the second pulse width adjustment circuit 413.

That is, when the sampling value received by the micro-processor is greater than the first threshold value, the micro-processor of the second pulse width adjustment circuit 413 directly controls the second pulse generator 414 via the duty cycle adjustment signal to reduce the duty cycle of the outputted pulse signal according to a preset manner in which the duty cycle of the outputted pulse signal is reduced. When the next cycle of the pulse signal comes, if the sampling value received by the microprocessor is still greater than the first threshold value, the microprocessor of the second pulse width adjustment circuit 413 further controls the second pulse generator 414 to reduce the duty cycle of the outputted pulse signal until the sampling value received by the micro-processor is less than or equal to the first threshold value. When the sampling value received by the microprocessor is greater than the second threshold value, the microprocessor of the second pulse width adjustment circuit 413 directly controls the second pulse generator 414 via the duty cycle adjustment signal to reduce the duty cycle of the outputted pulse signal according to a preset manner in which the duty cycle of the outputted pulse signal is reduced. When the next cycle of the pulse signal comes, if the duty cycle of the pulse signal does not fall to zero, the microprocessor of the second pulse width adjustment circuit 413 further controls the second pulse generator 414 to reduce the duty cycle of the outputted pulse signal until the pulse switching circuit stops working.

When the power supply circuit 1 and the pulse switching circuit 2 are used to output the unipolar pulse current to the load, the second pulse generator 414 may be configured to generate a fixed duty cycle pulse signal. When the power supply circuit 1 and the pulse switching circuit 2 are used to output bipolar pulse current to the load 101, the second pulse generator 414 may be a complementary symmetric PWM waveform generator capable of simultaneously generating and outputting a pair of pulse signals with the same frequency and duty cycle and 180 degrees out of phase. However, in some embodiments, the second pulse generator 414 may be configured to generate a pulse signal with an unfixed duty cycle.

Referring to FIG. 6, a control method of a pulse ablation instrument according to an embodiment of the present application includes steps of:

S01: sampling a current flowing through a power feeding loop of a load and obtaining a sampling value; and S02: reducing a duty cycle of a drive signal which controls an operation of a pulse switching circuit to reduce a current output to the load when the sampling value is greater than a threshold value.

The control method of a pulse ablation instrument according to an embodiment of the present application obtains the sampling value by sampling the current flowing through the load and the power feeding loop of the load, and when the sampling value is greater than the threshold value, reduces a duty cycle of the pulse signal, to reduce the current output to the load. Therefore, when the current flowing through the load and the power feeding loop of the load is excessive, the current flowing through the load and the power feeding loop of the load is reduced in real time, thereby protecting the switching components of the pulse switching circuit in the power feeding loop of the load, and preventing the switching components of the pulse switching circuit from being damaged by sustained large current shocks. Furthermore, the control method of a pulse ablation instrument according to the embodiment of the present application may also prevent the load from being subjected to large current for long periods of time, thereby avoiding harm to the load.

In particular, the control method of a pulse ablation instrument may be implemented by a processor. Referring to FIG. 7, in the control method of a pulse ablation instrument, the processor may first read a preset pulse parameter value, the preset pulse parameter value may include a preset duty cycle value, a preset frequency value, and the like. The processor then controls the pulse generator to output a pulse waveform according to the preset pulse parameter value. The sampling circuit then samples the current flowing through the power feeding loop of the load and obtains a sampling value and sends the sampling value to the processor, the processor receives, reads the sampling value and determines whether the sampling value exceeds a threshold value. When the sampling value reaches or exceeds the threshold value, the processor reduces a preset duty cycle value in the preset pulse parameter value and modifies a register that stores the preset pulse parameter value, and then the processor re-reads the modified preset pulse parameter value and controls the pulse generator to output the pulse waveform according to the modified preset pulse parameter value. When the sampling value does not reach and does not exceed the threshold value, the processor returns to the step of receiving and reading the sampling value, monitoring whether the sampling value reaches or exceeds the threshold value. Thus, the control method of a pulse ablation instrument achieves, in a software-controlled manner, real-time reduction of the current flowing through the load and the power feeding loop in which the load is located in the event of excessive current flowing through the load, to protect the power feeding loop and prevent the power feeding loop from being damaged by sustained large current shocks. Also, it may also prevent the load from being under large current for long periods of time, thereby avoiding harm to the load.

When the processor receives an external reset instruction, the preset pulse parameter value is reset to an initial value preset by the processor and the register is modified. Thus, after the control method of a pulse ablation instrument has reset the pulse ablation instrument, the pulse generator may be controlled to output a pulse waveform according to the initial value preset by the processor.

Referring to FIG. 8, in the control method of a pulse ablation instrument of some embodiments, the threshold value includes a first threshold value, and the step of reducing the duty cycle of the drive signal which controls an operation of the pulse switching circuit when the sampling value is greater than the threshold value (S02) includes a step of:

S021: reducing the duty cycle of the drive signal cycle by cycle until the sampling value is less than or equal to the first threshold value when the sampling value is greater than the first threshold value.

The first threshold value may correspond to a threshold that the sampling value exceeds when the load current is excessive, and specific value thereof may be referred to the above and will not be repeated here. The step of reducing the duty cycle of the drive signal cycle by cycle until the sampling value is less than or equal to the first threshold value includes determining whether the sampling value of the current cycle is less than or equal to the first threshold value and, when YES, stopping reducing the duty cycle of the drive signal; when NO, in the following next cycle continuing to reduce the duty cycle of the drive signal until the sampling value is less than or equal to the first threshold value. As such, the control method of a pulse ablation instrument achieves reducing the duty cycle of the drive signal when the current flowing through the power feeding loop of the load is excessive and thus reducing the current output to the load, until the current flowing through the power feeding loop to the load returns to normal, thereby achieving over current protection to the load and the power feeding loop of the load.

Referring to FIG. 9, in the control method of a pulse ablation instrument of some embodiments, the threshold value includes a first threshold value and a second threshold value, and the step of reducing the duty cycle of the drive signal which controls an operation of the pulse switching circuit when the sampling value is greater than the threshold value (S02) includes a step of:

S022: reducing the duty cycle of the drive signal cycle by cycle until the pulse switching circuit stops working when the sampling value is greater than the second threshold value, wherein the second threshold value is greater than the first threshold value.

The first threshold value may correspond to a threshold that the sampling value exceeds when the load current is excessive, and the second threshold value may correspond to a threshold that the sampling value exceeds when the load is short-circuited. Specific values of the first threshold value and the second threshold value may be referred to above and will not be repeated here. The step of reducing the duty cycle of the drive signal cycle by cycle until the pulse switching circuit stops working includes determining whether the duty cycle of the pulse signal for the current cycle falls to zero and, when YES, stopping reducing the duty cycle of the drive signal; when NO, continuing to reduce the duty cycle of the drive signal in the following cycle until the pulse switching circuit stops working. Therefore, in a state in which the power feeding loop of the load is short-circuited, the control method of a pulse ablation instrument can enable the current output to the load to be gradually reduced, turn off the switching component in a "soft landing" manner, which can prevent large transient changes in current from resulting in induced voltage spikes, and is advantageous in improving circuit safety of the process of turning off the pulse switching circuit when the load is short circuited, thereby achieving short circuit protection of the load and the power feeding loop of the load.

Referring to FIG. 10, in the control method of a pulse ablation instrument of some embodiments, the threshold value includes a first threshold value and a second threshold value, and the step of reducing the duty cycle of the drive signal which controls an operation of the pulse switching circuit when the sampling value is greater than the threshold value (S02) includes steps of:

S021: when the sampling value is greater than the first threshold value, reducing the duty cycle of the drive signal cycle by cycle until the sampling value is less than or equal to the first threshold value; and S022: when the sampling value is greater than the second threshold value, reducing the duty cycle of the drive signal cycle by cycle until the pulse switching circuit stops working, wherein the second threshold value is greater than the first threshold value.

The first threshold value may correspond to a threshold that the sampling value exceeds when the load current is excessive, and the second threshold value may correspond to a threshold that the sampling value exceeds when the load is short-circuited. Specific values of the first threshold value and the second threshold value may be referred to above and will not be repeated here. The step of reducing the duty cycle of the drive signal cycle by cycle until the sampling values are less than or equal to the first threshold value includes determining whether the sampling value of the current cycle is less than or equal to the first threshold value and, when YES, stopping reducing the duty cycle of the drive signal; when NO, continuing to reduce the duty cycle of the drive signal in the following cycle until the sampling value is less than or equal to the first threshold value. The step of reducing the duty cycle of the drive signal cycle by cycle until the pulse switching circuit stops working includes determining whether the duty cycle of the pulse signal for the current cycle falls to zero and, when YES, stopping reducing the duty cycle of the drive signal; when NO, continuing to reducing the duty cycle of the drive signal in the following cycle until the pulse switching circuit stops working. Therefore, when the current flowing through the power feeding loop of the load is excessive, the control method of a pulse ablation instrument reduces the duty cycle of the drive signal and reduces the current output to the load, until the current flowing through the power feeding loop of the load returns to normal, thereby providing over current protection to the load and the power feeding loop of the load. Further, in a state in which the power feeding loop of the load is short-circuited, the control method of a pulse ablation instrument can enable the current output to the load to be gradually reduced, turn off the switching component in a "soft landing" manner, which prevents large transient changes in current from resulting in induced voltage spikes, thereby advantageously improving circuit safety of the process of turning off the pulse switching circuit when the load is short circuited, and achieving short-circuit protection of the load and the power feeding loop of the load.

In summary, the pulse ablation instrument and control method, control apparatus thereof, electronic device, and media of embodiments of the present application sample the current flowing through the load and the power feeding loop of the load, and reduce the duty cycle of the pulse signal to reduce the current output to the load when the sampling value is greater than the threshold value, therefore, when the current flowing through the load and the power feeding loop of the load is excessive, the current flowing through the load and the power feeding loop of the load is reduced in real time, thereby protecting the switching components of the pulse switching circuit in the power feeding loop of the load, and preventing the switching components of the pulse switching circuit from being damaged by sustained large current shocks. Furthermore, the pulse ablation instrument and control method, control apparatus thereof, electronic device, and media in accordance with embodiments of the present application may also prevent the load from being subjected to large current for long periods of time, thereby avoiding harm to the load.

In the descriptions of the embodiments of the present application, any process or method descriptions in flow charts or otherwise described herein can be understood as, modules, segments, or portions of code which represent one or more executable instructions for implementing specific logical functions or steps of a process, and the scope of the preferred embodiments of the present application includes additional implementations in which functions may be executed out of order from that shown or discussed, including simultaneous order or in reverse order, according to the functionality involved, as would be understood by those skilled in the art to which embodiments of the present application belongs.

Logic and/or steps represented in flow charts or otherwise described herein, for example, it can be considered a sequence listing of executable instructions for implementing logical functions, embodied in any computer-readable medium for use by or in connection with an instruction execution system, apparatus, or device (such as a computer-based system, system that includes a processing module, or other system that can fetch the instructions from the instruction execution system, apparatus, or device and execute the instructions). For the purpose of this specification, a "computer-readable medium" can be any apparatus that can contain, store, communicate, propagate or transport the program for use by or in connection with the instruction execution system, apparatus, or device. More specific examples (a non-exhaustive list) of the computer-readable medium include the following: an electrical connection having one or more wires (control methods), a portable computer diskette (magnetic device), a random-access memory (RAM), a read-only memory (ROM), an erasable programmable read-only memory (EPROM or Flash memory), an optical fiber device, and a portable compact disc read-only memory (CDROM). In addition, the computer readable medium could even be paper or other suitable medium onto which the program can be printed, as the program can be electronically obtained, for example, by optically scanning the paper or other medium, followed by editing, interpreting, or otherwise processing in a suitable manner as necessary, and then stored in a computer memory.

It should be understood that portions of the embodiments of the present application may be implemented in hardware, software, firmware, or a combination thereof. In the embodiments described above, various steps or methods can be implemented in software or firmware stored in a memory and executed by a suitable instruction execution system. For example, if implemented in hardware, as in another embodiment, it may be implemented with any or a combination of the following technologies well known in the art: a discrete logic circuit having logic gates for implementing logic functions on data signals, an application specific integrated circuit having suitable combinational logic gates, a programmable gate array (PGA), a field programmable gate array (FPGA), etc.

Although the above description is to be construed as exemplary embodiments of the present application, the scope of the present application is not intended to be limited thereto, and any modification or substitution readily apparent to those skilled in the art, shall be within the scope of the present application. Therefore, the protection scope of the present application should be subject to the protection scope of the claims.

The invention claimed is:

1. A pulse ablation instrument comprising:
   a power supply circuit, configured to supply power to a load;
   a pulse switching circuit, connected to the power supply circuit to regulate a current output by the power supply circuit and flowing to the load;
   a sampling circuit configured to sample a current flowing through a power feeding loop of the load and obtain a sampling value; and
   a switching control circuit, electrically connected to the sampling circuit and the pulse switching circuit, and configured to output a drive signal which controls an operation of the pulse switching circuit according to the sampling value and reduce a duty cycle of the drive signal to reduce an output current of the power supply circuit when the sampling value is greater than a threshold value; and
   wherein the sampling circuit comprises one or more current transformers, each current transformer comprises a primary winding and a secondary winding; the primary winding is connected in series with the power feeding loop of the load, and the secondary winding is electrically connected with the switching control circuit, the secondary winding is configured to output the sampling value.

2. The pulse ablation instrument of claim 1, wherein the threshold value comprises a first threshold value and a second threshold value, and wherein
   when the sampling value is greater than the first threshold value, the switching control circuit reduces the duty cycle of the drive signal cycle by cycle until the sampling value is less than or equal to the first threshold value; or
   when the sampling value is greater than the second threshold value, the switching control circuit reduces the duty cycle of the drive signal cycle by cycle until the pulse switching circuit stops working; or
   when the sampling value is greater than the first threshold value, the switching control circuit reduces the duty cycle of the drive signal cycle by cycle until the sampling value is less than or equal to the first threshold value; and when the sampling value is greater than the second threshold value, the switching control circuit reduces the duty cycle of the drive signal cycle by cycle until the pulse switching circuit stops working, wherein the second threshold value is greater than the first threshold value.

3. The pulse ablation instrument of claim 2, wherein the switching control circuit comprises:
   a pulse regulating circuit, configured to generate a pulse signal and adjust a duty cycle of the pulse signal according to the sampling value; and
   a drive circuit, configured to receive the pulse signal and output the drive signal according to the pulse signal, wherein the duty cycle of the drive signal varies as a function of the duty cycle of the pulse signal.

4. The pulse ablation instrument of claim 3, wherein the pulse regulating circuit comprises:
   a first pulse generator, configured to generate the pulse signal; and
   a first pulse width adjustment circuit, electrically connected to the first pulse generator, the sampling circuit, and the drive circuit and configured to receive the pulse signal and adjust the duty cycle of the pulse signal according to the sampling value.

5. The pulse ablation instrument of claim 4, wherein the first pulse width adjustment circuit comprises:
   a pulse regulating first sub-circuit, configured to determine whether the sampling value is greater than the first threshold value according to the sampling value inputted, and reduce the duty cycle of the pulse signal cycle by cycle until the sampling value is less than or equal to the first threshold value when the sampling value is greater than the first threshold value.

6. The pulse ablation instrument of claim 4, wherein the first pulse width adjustment circuit comprises:
   a comparator, wherein a non-inverting input terminal of the comparator receives the sampling value, an inverting input terminal of the comparator receives the second threshold value, when the sampling value is greater than the second threshold value, the comparator outputs a trigger level;

a flip-flop, configured to receive the trigger level and output a control signal; and a pulse regulating second sub-circuit, configured to reduce the duty cycle of the pulse signal cycle by cycle according to the control signal until the duty cycle of the pulse signal falls to zero.

7. The pulse ablation instrument of claim 6, further comprising a main control unit, wherein the main control unit controls an alarm unit to alarm when the sampling value is greater than the second threshold value; the main control unit is further configured to send a reset signal to the flip-flop according to an external reset instruction to cause the flip-flop to reset and stop outputting the control signal.

8. The pulse ablation instrument of claim 3, wherein the pulse regulating circuit comprises:

a second pulse width adjustment circuit, electrically connected to the sampling circuit and configured to generate a duty cycle adjustment signal according to the sampling value; and a second pulse generator, electrically connected to the second pulse width adjustment circuit and the drive circuit, and configured to generate a pulse signal according to the duty cycle adjustment signal, wherein the duty cycle of the pulse signal is adjusted by the duty cycle adjustment signal.

9. The pulse ablation instrument of claim 3, wherein the power supply circuit comprises a first DC power source; the pulse switching circuit comprises a first pulse switching component;

a first terminal of the first pulse switching component is connected to a positive pole of the first DC power source, a second terminal of the first pulse switching component is connected to a first terminal of the load, a second terminal of the load is connected to a negative pole of the first DC power source, and a control terminal of the first pulse switching component is connected to an output terminal of the drive circuit.

10. The pulse ablation instrument of claim 9, wherein the power supply circuit further comprises a second DC power source, a positive pole of the second DC power source is connected to the second terminal of the load and the negative pole of the first DC power source;

the pulse switching circuit further comprises a second pulse switching component, a first terminal of the second pulse switching component is connected to the first terminal of the load, a second terminal of the second pulse switching component is connected to the negative pole of the second DC power source, and a control terminal of the second pulse switching component is connected to the drive circuit;

the pulse regulating circuit is configured to generate a first pulse signal and a second pulse signal, the drive circuit comprises a first drive circuit and a second drive circuit;

an output terminal of the first drive circuit is connected to the control terminal of the first pulse switching component, the first drive circuit is configured to receive the first pulse signal and output a first drive signal to drive an operation of the first pulse switching component; and an output terminal of the second drive circuit is connected to the control terminal of the second pulse switching component, the second drive circuit is configured to receive the second pulse signal and output a second drive signal to drive an operation of the second pulse switching component.

11. The pulse ablation instrument of claim 10, wherein both of the first pulse switching component and the second pulse switching component are IGBT transistors; or both of the first pulse switching component and the second pulse switching component are MOS transistors.

12. The pulse ablation instrument of claim 1, wherein the sampling circuit further comprises a voltage dividing circuit, the voltage dividing circuit comprises a first resistor and a second resistor which are connected in series between an output terminal of the secondary winding of the current transformer and a ground terminal, a connection point where the first resistor and the second resistor are connected together outputs the sampling value.

13. A control method of a pulse ablation instrument according to claim 1, comprising steps of:

sampling a current flowing through a power feeding loop of a load and obtaining a sampling value; and reducing a duty cycle of a drive signal which controls an operation of a pulse switching circuit to reduce a current output to the load when the sampling value is greater than a threshold value.

14. The control method of a pulse ablation instrument of claim 13, wherein the threshold value comprises a first threshold value and/or a second threshold value, the step of reducing a duty cycle of a drive signal which controls an operation of a pulse switching circuit when the sampling value is greater than a threshold value comprises steps of:

reducing the duty cycle of the drive signal cycle by cycle until the sampling value is less than or equal to the first threshold value when the sampling value is greater than the first threshold value; and/or reducing the duty cycle of the drive signal cycle by cycle until the pulse switching circuit stops working when the sampling value is greater than the second threshold value, wherein the second threshold value is greater than the first threshold value.

15. An electronic device comprising:

a processor; and a memory, configured to store executable instructions of the processor;

wherein the processor is configured to execute the executable instructions to perform the control method of a pulse ablation instrument of claim 13.

16. A computer readable medium having stored a computer program thereon which, when executed by a processor, implements a control method of a pulse ablation instrument according to claim 13.

17. The computer readable medium of claim 16, wherein the threshold value comprises a first threshold value and a second threshold value, the step of reducing a duty cycle of a drive signal which controls an operation of a pulse switching circuit when the sampling value is greater than a threshold value comprises a step of:

reducing the duty cycle of the drive signal cycle by cycle until the sampling value is less than or equal to the first threshold value when the sampling value is greater than the first threshold value; and/or reducing the duty cycle of the drive signal cycle by cycle until the pulse switching circuit stops working when the sampling value is greater than the second threshold value, wherein the second threshold value is greater than the first threshold value.

18. A pulse ablation instrument comprising:

a power supply circuit, configured to supply power to a load;

a pulse switching circuit, connected to the power supply circuit to regulate a current output by the power supply circuit and flowing to the load;

a sampling circuit configured to sample a current flowing through a power feeding loop of the load and obtain a sampling value; and a switching control circuit, electrically connected to the sampling circuit and the pulse switching circuit, and configured to output a drive signal which controls an operation of the pulse switching circuit according to the sampling value and reduce a duty cycle of the drive signal to reduce an output current of the power supply circuit when the sampling value is greater than a threshold value; and wherein the switching control circuit comprises:

a pulse regulating circuit, configured to generate a pulse signal and adjust a duty cycle of the pulse signal according to the sampling value; and a drive circuit, configured to receive the pulse signal and output the drive signal according to the pulse signal, wherein the duty cycle of the drive signal varies as a function of the duty cycle of the pulse signal; and wherein the pulse regulating circuit comprises:

a second pulse width adjustment circuit, electrically connected to the sampling circuit and configured to generate a duty cycle adjustment signal according to the sampling value; and a second pulse generator, electrically connected to the second pulse width adjustment circuit and the drive circuit, and configured to generate a pulse signal according to the duty cycle adjustment signal, wherein the duty cycle of the pulse signal is adjusted by the duty cycle adjustment signal.

19. A pulse ablation instrument comprising:

a power supply circuit, configured to supply power to a load;

a pulse switching circuit, connected to the power supply circuit to regulate a current output by the power supply circuit and flowing to the load;

a sampling circuit configured to sample a current flowing through a power feeding loop of the load and obtain a sampling value; and a switching control circuit, electrically connected to the sampling circuit and the pulse switching circuit, and configured to output a drive signal which controls an operation of the pulse switching circuit according to the sampling value and reduce a duty cycle of the drive signal to reduce an output current of the power supply circuit when the sampling value is greater than a threshold value; and wherein the switching control circuit comprises:

a pulse regulating circuit, configured to generate a pulse signal and adjust a duty cycle of the pulse signal according to the sampling value; and a drive circuit, configured to receive the pulse signal and output the drive signal according to the pulse signal, wherein the duty cycle of the drive signal varies as a function of the duty cycle of the pulse signal; and wherein the power supply circuit comprises a first DC power source; the pulse switching circuit comprises a first pulse switching component; a first terminal of the first pulse switching component is connected to a positive pole of the first DC power source, a second terminal of the first pulse switching component is connected to a first terminal of the load, a second terminal of the load is connected to a negative pole of the first DC power source, and a control terminal of the first pulse switching component is connected to an output terminal of the drive circuit.

\* \* \* \* \*